(12) United States Patent
Santangelo et al.

(10) Patent No.: US 9,387,025 B2
(45) Date of Patent: Jul. 12, 2016

(54) BONE SCREW AND SELF-RETAINING DRIVER

(75) Inventors: Stephen Anthony Santangelo, Sturbridge, MA (US); Jeffrey Wyman, Naples, FL (US); Neil J. Etherington, Logan, UT (US); Pascal Boileau, Nice (FR)

(73) Assignee: Smith & Nephew, Inc., Memphis, TN (US)

( * ) Notice: Subject to any disclaimer, the term of this patent is extended or adjusted under 35 U.S.C. 154(b) by 287 days.

(21) Appl. No.: 13/439,099

(22) Filed: Apr. 4, 2012

(65) Prior Publication Data
US 2013/0268010 A1 Oct. 10, 2013

(51) Int. Cl.
*A61B 17/86* (2006.01)
*A61B 17/88* (2006.01)
*A61B 17/00* (2006.01)

(52) U.S. Cl.
CPC ........... *A61B 17/8615* (2013.01); *A61B 17/862* (2013.01); *A61B 17/8883* (2013.01); *A61B 17/8888* (2013.01); *A61B 17/864* (2013.01); *A61B 17/8897* (2013.01); *A61B 2017/0042* (2013.01); *A61B 2017/00389* (2013.01)

(58) Field of Classification Search
CPC ............. A61B 17/8875; A61B 17/808; A61B 17/8872
USPC ........................................................ 411/910
See application file for complete search history.

(56) References Cited

U.S. PATENT DOCUMENTS

| | | | | |
|---|---|---|---|---|
| 5,370,662 | A | * 12/1994 | Stone et al. | 606/232 |
| 6,033,405 | A | 3/2000 | Winslow et al. | |
| 6,302,887 | B1 | * 10/2001 | Spranza et al. | 606/916 |
| 6,342,055 | B1 | 1/2002 | Eisermann et al. | |
| 6,436,100 | B1 | * 8/2002 | Berger | 606/916 |
| 6,755,836 | B1 | 6/2004 | Lewis | |

(Continued)

FOREIGN PATENT DOCUMENTS

| | | |
|---|---|---|
| WO | 03063714 A2 | 8/2003 |
| WO | 2006023793 A2 | 3/2006 |
| WO | 2009052294 A1 | 4/2009 |

OTHER PUBLICATIONS

International Search Report for PCT/US2013/034984 dated Oct. 10, 2013.

(Continued)

*Primary Examiner* — Samuel Hanna
(74) *Attorney, Agent, or Firm* — Burns & Levinson LLP; Joseph M. Maraia

(57) ABSTRACT

Techniques disclosed herein include systems and methods for a bone screw and self-retaining driver. The system includes a mechanism that enables a bone screw to be rigidly attached to a screwdriver for manipulation and transfer of bone fragments and grafts to a fixation site, such as during surgery. The system includes a cannulated bone screw that has a drive connection that engages with a drive structures of a screwdriver. The bone screw also includes a structural connector that securely attaches to or receives an internal shaft or rod of the screwdriver. The internal shaft or rod of the screwdriver can rotate and slide independent of an outer shaft of screwdriver. Accordingly, the internal shaft of the screwdriver can rigidly connect with the bone screw enabling applied torque to the screwdriver to be transferred to the bone screw, without the bone screw falling off of the drive connection.

13 Claims, 6 Drawing Sheets

(56) References Cited

U.S. PATENT DOCUMENTS

| | | |
|---|---|---|
| 7,235,079 B2 | 6/2007 | Jensen et al. |
| 2004/0225292 A1 | 11/2004 | Sasso et al. |
| 2006/0149264 A1 | 7/2006 | Castaneda et al. |
| 2007/0038221 A1 | 2/2007 | Fine et al. |
| 2007/0043379 A1 | 2/2007 | Sullivan, Jr. et al. |
| 2008/0065070 A1* | 3/2008 | Freid et al. .................. 606/61 |
| 2008/0275456 A1* | 11/2008 | Vonwiller .......... A61B 17/7032 606/246 |
| 2009/0187194 A1* | 7/2009 | Hamada ........................ 606/104 |
| 2009/0326545 A1* | 12/2009 | Schaffhausen ..... A61B 17/8891 606/104 |
| 2010/0185246 A1 | 7/2010 | Castañeda et al. |
| 2010/0217333 A1 | 8/2010 | McShane et al. |
| 2010/0298892 A1* | 11/2010 | Biyani et al. .................. 606/318 |
| 2011/0093020 A1 | 4/2011 | Wu |
| 2011/0098715 A1 | 4/2011 | Laubert et al. |
| 2011/0190830 A1 | 8/2011 | Biedermann et al. |

OTHER PUBLICATIONS

Written Opinion for PCT/US2013/034984 dated Oct. 4, 2014.

Communication pursuant to Article 94(3) EPC from related European Application No. 13716926.6 dated Nov. 25, 2015.

\* cited by examiner

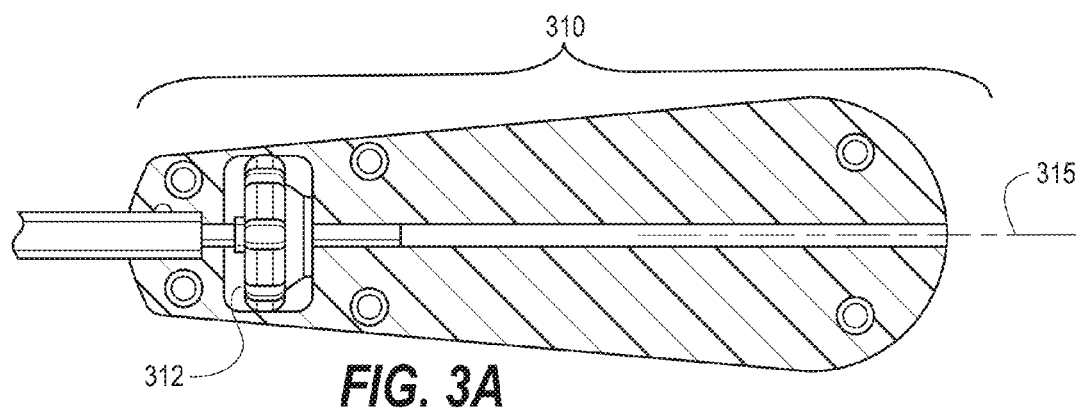
FIG. 3A
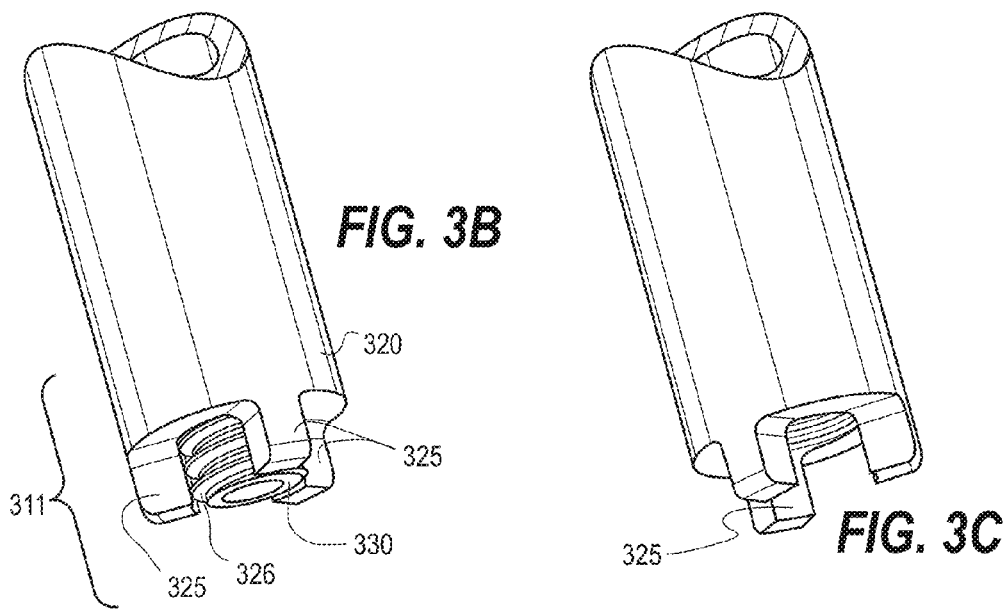
FIG. 3B
FIG. 3C
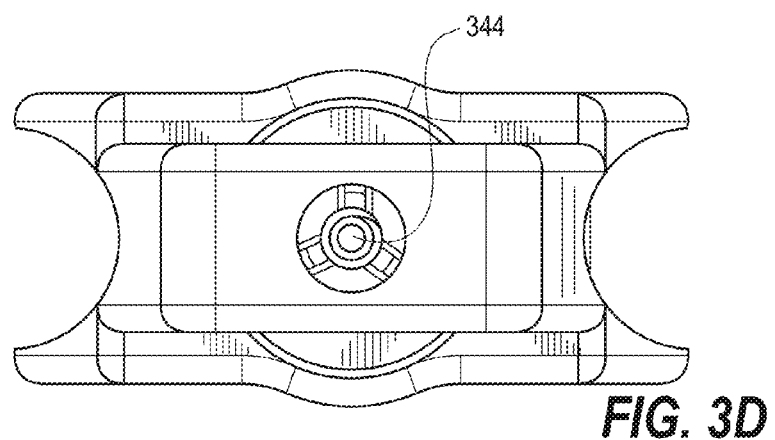
FIG. 3D

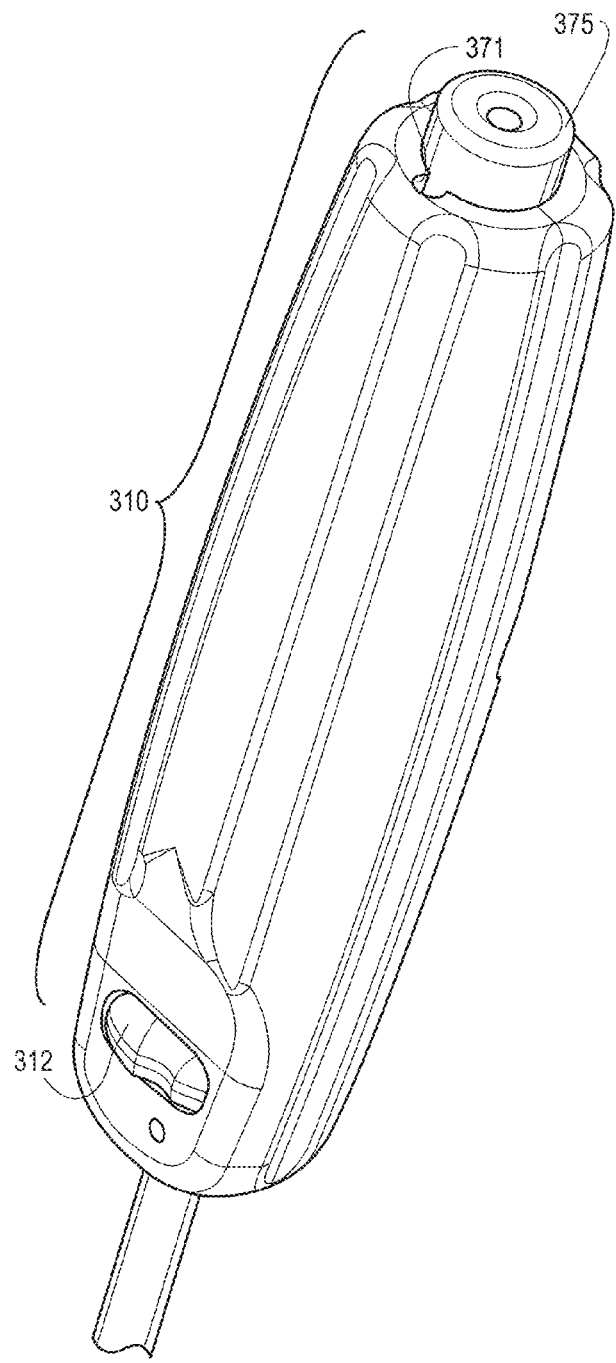
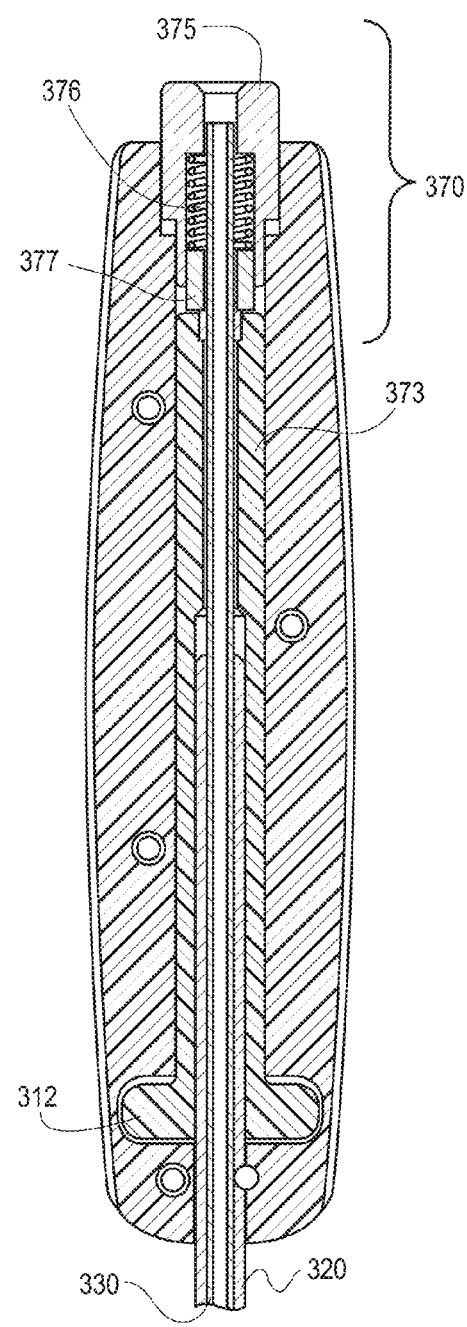
FIG. 5                    FIG. 6

BONE SCREW AND SELF-RETAINING DRIVER

BACKGROUND

The present disclosure relates to tools and methods for use in surgery including arthroscopic surgery.

Conventional screw or fastener driving devices provide different ways of holding a screw in position while the screw is driven into a work material such as a wall, wood, bone, etc. Some drivers include a mechanism to retain a screw against a driver head. Conventional self-retaining bone screwdrivers, however, typically do not have active engagement mechanisms. Most drivers have a passive retaining mechanism that can lead to unintentional disengagement from the driver. For example, one type of conventional screwdriver includes a magnetized driving bit to hold a respective metal screw to the bit during installation. While the magnetic driving bit can initially hold the screw inline with the driver shaft, the driving bit may have poor holding power. As a result, the screw can easily tilt to an undesirable angle when uneven force is applied on the head of the screw, and even disengage from the driver. Other passive retaining mechanisms can have the same drawbacks as a magnetized driving bit in that there is a significant possibility of disengagement. During surgery, having a passive engagement mechanism with a significant risk of disengagement is not acceptable as bone screws could be lost in a surgery site. Drivers with active retaining mechanisms also have drawbacks. Active retaining mechanisms can be cumbersome, use a wider diameter screw/screwdriver, require excessive force to engage/disengage, or have other drawbacks. What is needed, therefore, is a self-retaining bone screwdriver using an active engagement mechanism that is compact and easy to use.

SUMMARY

Techniques disclosed herein include a novel bone screw and self-retaining driver system and method. The bone screw and self-retaining driver embodiments include a screw and a screwdriver system. The screwdriver system has two shafts. One shaft is an outer shaft that is tubular and has a proximal end that is secured to a handle and a distal end that defines a tip. The tip at the distal end of the outer shaft can be shaped to mate or engage with a head of the bone screw. In one example, the bone screw head can define a tri-lobe recess area into which a correspondingly shaped tri-lobe tip of the outer shaft of the driver can be inserted. This construction allows the bone screw to be rotationally torqued by the tip of the outer shaft when the tip is engaged with the screw head.

The driver also includes an internal shaft or rod that extends through the central axis of the tube defined by the outer cylindrical shaft. A distal end of this inner rod can include a male threaded tip. The driver handle defines an opening to expose a thumb wheel or other control mechanism secured to the inner rod. The thumbwheel enables a user holding the handle to rotate the inner rod independently of rotation of the outer shaft. The inner rod can also be configured to slide a short distance back and forth within the tube defined by the outer shaft, that is, slide in a longitudinal direction. When the inner rod is slid towards the distal end of the outer shaft, the threaded tip at the distal end of the inner rod is exposed out of an opening defined in the center of the tri-lobed tip of the outer shaft of the driver. When the threaded end of the inner rod is exposed in this manner, a user holding the bone screw can rotate the thumbwheel to cause the threaded tip of the inner rod to engage with, and secure to, a corresponding threaded shaft defined in the head of the screw. This action draws the screw onto the driver and causes engagement of the tri-lobed tip of the outer shaft into the tri-lobed recess area of the head of the screw. When fully engaged, the screw is rigidly secured to the driver. Since the screw is rigidly attached to the driver when fully engaged in this manner, the screw can be screwed into a bone fragment or bone media, and the driver can operate as a manipulator enabling precise placement and advancement of the bone screw.

Another feature is that the diameter of the outer shaft of the driver is similar to (in some embodiments, equal to or greater than) the diameter of the screw's head. This allows a screw that is threaded and secured onto the tip of the driver to be disposed through a cannula for insertion into a body of a patient undergoing an endoscopic procedure or other surgery procedure.

Another feature is that the bone screw head includes a concavity on its underside (the side of the screw head that faces the material (e.g. bone) to which the screw is being secured. This concavity extends across the underside surface of the screw head from an outer lower edge of the screw head towards the shaft of the screw head. This results in the screw head having an outer lower edge that first contacts and secures to a surface of the bone fragment when the screw is fully torqued and inserted (i.e. screwed in) to bone media. This screw head design causes less fracturing of the bone material when the screw is tightened fully into the bone fragment.

In another embodiment, a bone screw includes an elongated member having a distal end, a proximal end, and a longitudinal axis. At least a portion of the distal end has external threading adapted to advance the bone screw into bone media. The proximal end has a force-receiving structure configured to receive applied torque. The bone screw is cannulated in that it defines a passage or lumen that follows the longitudinal axis of the bone screw. The defined passage is sized to enable the bone screw to travel along a guide wire. The proximal end of the bone screw defines a socket having internal threading. The defined socket is aligned with the defined passage.

Continuing with this embodiment, a bone screwdriver includes a shaft portion connected to a handle portion. The shaft portion includes an external shaft and an internal shaft. The internal shaft is positioned within the external shaft. The internal shaft is configured to rotate independent of the external shaft. A distal end of the external shaft has a force-transfer structure configured to transfer applied torque to the force-receiving structure of the bone screw when in contact with the force-receiving structure. A distal end of the internal shaft has external threading adapted to advance into the defined socket of the bone screw such that when advanced into internal threading of the defined socket, the bone screw is securely attached to the bone screwdriver via the internal shaft. This attachment is such that the force-transfer structure is in contact with the force-receiving structure. The handle portion includes a rotation mechanism that controls rotation of the internal shaft independent of the external shaft. The bone screwdriver is cannulated in that the bone screwdriver defines a passage that follows a longitudinal axis of the bone screwdriver such that the bone screwdriver can travel along a guide wire.

Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

Note that this summary section herein does not specify every embodiment and/or incrementally novel aspect of the present disclosure or claimed invention. Instead, this summary only provides a preliminary discussion of different embodiments and corresponding points of novelty over conventional techniques. For additional details and/or possible perspectives of the invention and embodiments, the reader is directed to the Detailed Description section and corresponding figures of the present disclosure as further discussed below.

BRIEF DESCRIPTION OF THE DRAWINGS

The foregoing and other objects, features, and advantages of the invention will be apparent from the following more particular description of preferred embodiments herein as illustrated in the accompanying drawings in which like reference characters refer to the same parts throughout the different views. The drawings are not necessarily to scale, with emphasis instead being placed upon illustrating the embodiments, principles and concepts.

FIG. 3A is an example perspective view of a handle portion of a screwdriver according to embodiments herein.

FIG. 3B is an example perspective view of a tip portion of a screwdriver with internal shaft extended according to embodiments herein.

FIG. 3C is an example perspective view of a tip portion of a screwdriver with internal shaft retracted according to embodiments herein.

FIG. 3D is an example view of a proximal end of the screwdriver according to embodiments herein.

FIG. 5 is an example perspective view of a handle portion of a self-retaining driver system for a bone screw according to embodiments herein.

FIG. 6 is an example side cross-sectional view of a handle portion of a self-retaining driver system for a bone screw according to embodiments herein.

DETAILED DESCRIPTION

Techniques disclosed herein include a novel bone screw and self-retaining driver system and method. In general, the system includes a mechanism that enables a bone screw to be rigidly attached to a screwdriver for manipulation and transfer of bone fragments and grafts to a fixation site, such as during surgery. The system includes a cannulated bone screw that has a drive connection that engages with a drive structure of a screwdriver. The bone screw also includes a structural connector that securely attaches to or receives an internal shaft or rod of the screwdriver. The internal shaft or rod of the screwdriver can rotate and slide independent of an outer shaft of the screwdriver. Accordingly, the internal shaft of the screwdriver can rigidly connect with the bone screw such that the drive connections of the bone screw and screwdriver are in contact enabling an applied torque to the screwdriver to be transferred to the bone screw, without the bone screw falling off of the drive connection. After advancing the bone screw into a target medium, the internal shaft can be disengaged with the bone screw so that the screwdriver can disengage with the bone screw. Both the bone screw and screwdriver can be cannulated to enable sliding along a guide wire.

Figure 1:
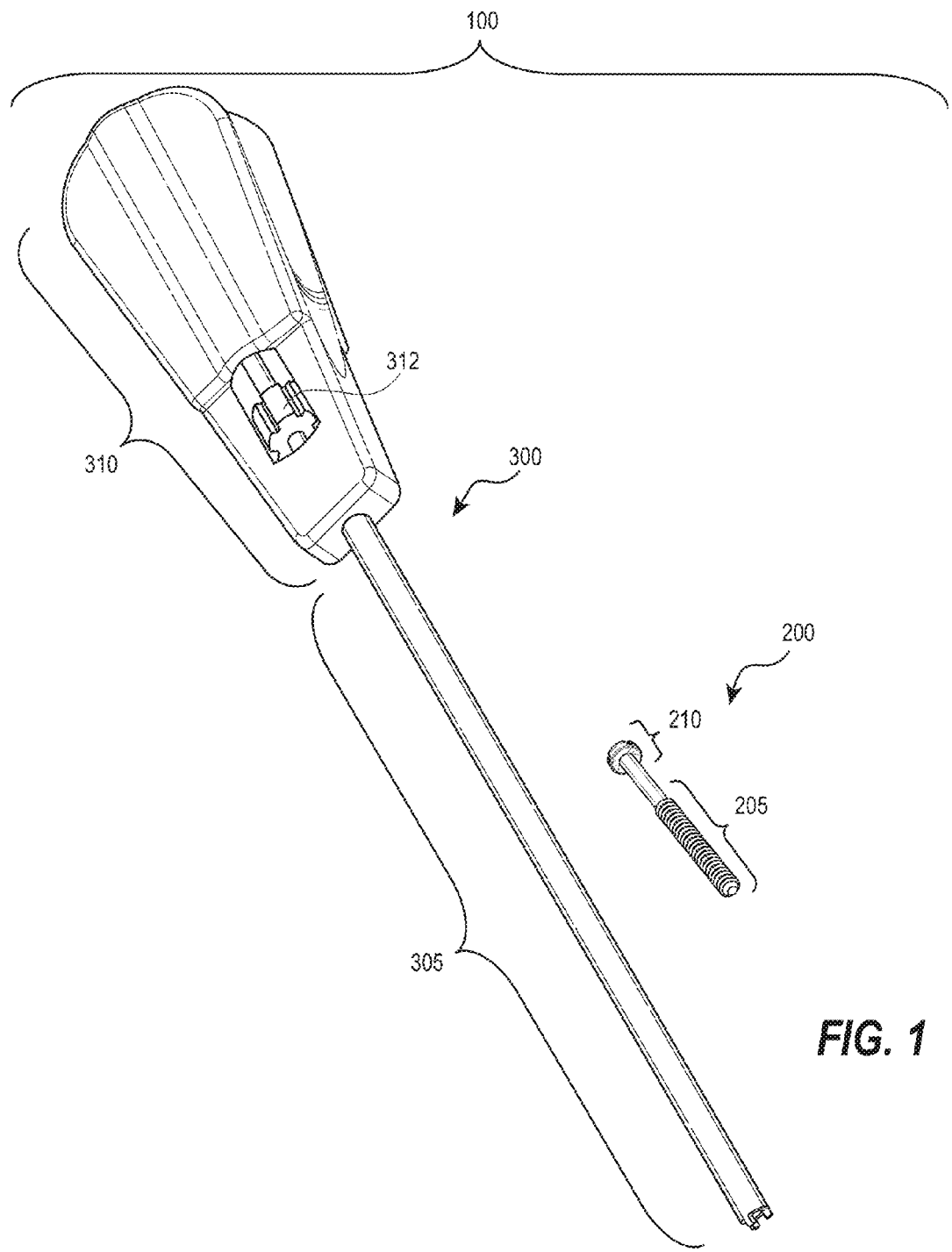
FIG. 1 is an example perspective view of a bone screw and self-retaining driver system according to embodiments herein.

FIG. 1 illustrates an example perspective view of a bone screw and self-retaining driver system 100. This system includes bone screw 200 and screwdriver 300. The bone screw 200 and screwdriver 300 include an active self-retaining mechanism that securely and rigidly connects the bone screw 200 to a tip of screwdriver 300. This secure attachment is such that the bone screw 200 can be driven into bone or other media without requiring manually holding the bone screw 200 on the tip of the screwdriver 300. The active self-retaining mechanism can be released after fully or partially advancing the bone screw 200 into bone media.

Referring to FIGS. 1, 2A, 2B, and 2C, the bone screw includes an elongated member having a distal end 205, a proximal end 210, and a longitudinal axis 215. The elongated member is generally cylindrical, though other cross-sectional shaft shapes can be used. Note that reference to a distal end and proximal end is helpful to identify features located at approximately those locations or ends. At least a portion of the distal end 205 has external threading 220 adapted to advance the bone screw into bone media. In some embodiments external threading 220 can extend or cover essentially the entire bone screw 200, while in other embodiments the external threading 220 covers just a portion of the elongated member or shaft in general. External threading geometry can be based on a particular media of use, or a particular application.

Figure 2A:
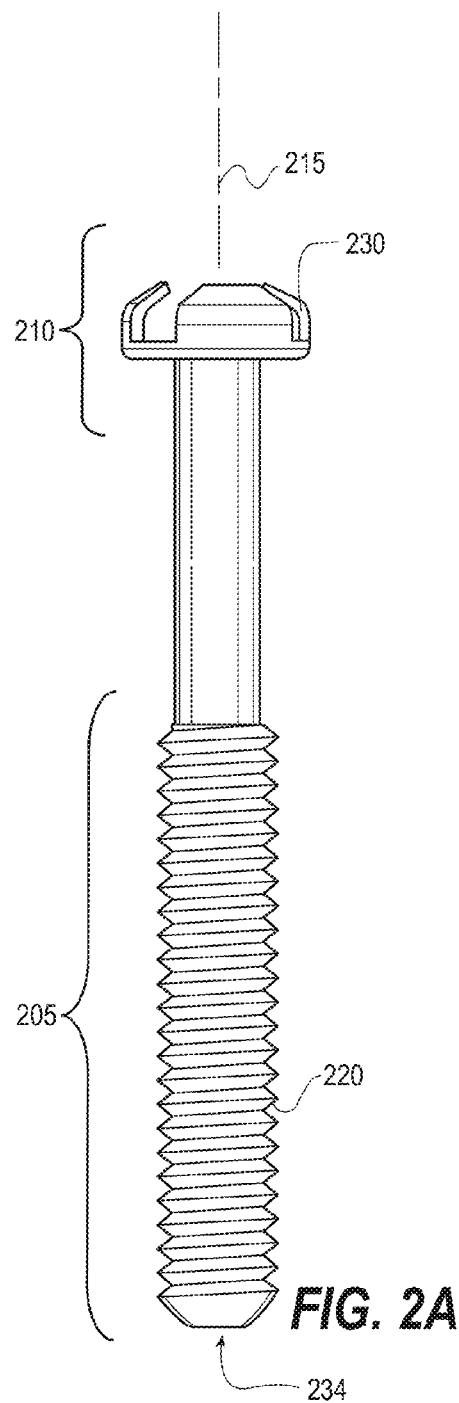
FIG. 2A is an example side view of a bone screw according to embodiments herein.
Figure 2B:
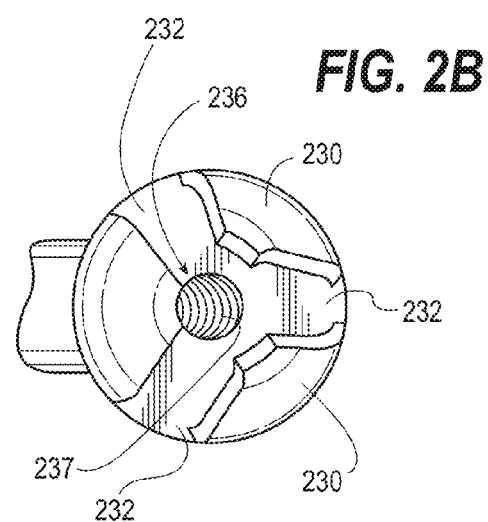
FIG. 2B is an example top perspective view of a bone screw according to embodiments herein.

The proximal end 210 or head of bone screw 200 has a force-receiving structure 230, configured to receive applied torque. Typically the applied torque will be transferred to the bone screw 200 from screwdriver 300. The force-receiving structure 230 can have various shapes, sizes and configurations. FIG. 2B shows force-receiving structure 230 defining slots 232. In this example there are three of slots 232, defined essentially by protrusions/structures in the proximal portion 210 of the bone screw 200. In other embodiments there may be a single slot or at least two slots. Note that instead of defining slots, the force-receiving structure can instead define a number of lobes as recessed features for accepting the screwdriver 300, such as three or more lobes sized and shaped to connect with corresponding lobe structures of the external shaft of the screwdriver 300. Moreover, the force-receiving structure can be embodied as any pentagon, lobe, or slot arrangement, including conventional drive geometry. In some embodiments, the force-receiving structure is a recessed design having a shape that corresponds to the force-transfer structure of the bone screwdriver.

The bone screw 200 is cannulated is that the bone screw 200 defines a passage 234 or lumen that follows the longitudinal axis 215. The defined passage 234 is sized to enable the bone screw 200 to travel along a guide wire (not shown). Guide wires are commonly used in arthroscopic procedures.

Typically a surgeon will place a guide wire at a site to be accessed again or to add fixation devices. The guide wire helps to ensure that additional items or instruments can safely and easily access a particular site without straying or disrupting surrounding tissue. Thus, the defined passage is sufficient for a guide wire to pass through the length of the bone screw 200.

Figure 2C:
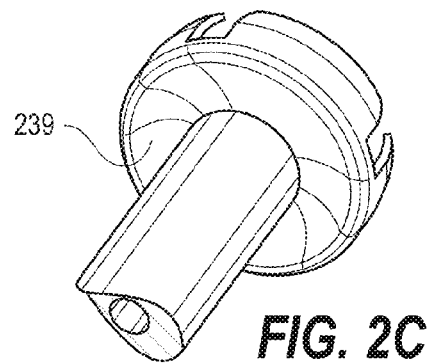
FIG. 2C is an example bottom perspective view of a bone screw according to embodiments herein.

The proximal end 210 of bone screw 200 defines a socket 236 having internal threading 237. Note that for this example embodiment, screw threading is used, but other embodiments can use snap fasteners, ball and socket mechanisms, etc. The defined socket 236 is aligned with the defined passage. For example, the defined socket 236 can be concentric with the defined passage, sharing a longitudinal axis. The defined socket can also be centered with the force-receiving structure. In most embodiments, the defined socket can have a larger diameter than the passage 234, but this is not required. FIG. 2C illustrates concave surface 239, which is essentially a bottom side of the screw head. With such curvature, an outside edge of the bone screw head first contacts bone media before a surface adjacent to the shaft.

Referring now to FIGS. 1, 3A, 3B, 3C, and 3D, the bone screwdriver 300 includes a shaft portion 305 connected to a handle portion 310. The shaft portion 305 includes an external shaft 320 and an internal shaft 330. The internal shaft 330 is positioned within the external shaft 320. The internal shaft 330 is configured to rotate independent of the external shaft 320. The external shaft 320 can be fixedly connected to handle portion 310. Thus, the external shaft defines a longitudinal space or cavity within which the internal shaft can rotate and slide. A distal end 311 (driver tip) of the external shaft 320 has a force-transfer structure 325 configured to transfer applied torque to the force-receiving structure 230 of the bone screw 200 when in contact with the force-receiving structure 230. A distal end 311 of the internal shaft 330 has external threading 326 adapted to advance into the defined socket 236 of the bone screw 200 such that when advanced into internal threading 237 of the defined socket 236, the bone screw 200 is securely attached to the bone screwdriver 300 via the internal shaft 330 such that the force-transfer structure 325 is in contact with the force-receiving structure 230. The handle portion 310 includes a rotation mechanism 312 that controls rotation of the internal shaft 330 independent of the external shaft 320. The rotation mechanism 312 can be a rotatable wheel, a lever, or other manually controlled mechanism that controls the internal shaft 330. The rotation mechanism can be framed within an opening defined by or within handle portion 310. The rotation mechanism 312 can also slide longitudinally with the handle portion 310 or defined window. Sliding the rotation mechanism 312 within the framed opening causes the internal shaft 330 to travel longitudinally within the external shaft 320. The amount of travel can be sufficient for the internal shaft 330 to retract within the external shaft 320, and to extend to couple with the defined socket 236.

The bone screwdriver 300 is configured as cannulated through its entire longitudinal axis by defining a passage 344 that follows a longitudinal axis 315 of the bone screwdriver 300 such that the bone screwdriver 300 can travel along a guide wire. Moreover, the self-retaining mechanism is configured such that when the bone screw 200 is being securely retained by the bone screwdriver 300, the coupled system (screw retained by driver) still provides a passage or lumen for sliding along a guide wire, essentially following a same longitudinal axis through the handle 310, internal shaft 330, and bone screw 200.

Figure 4A:
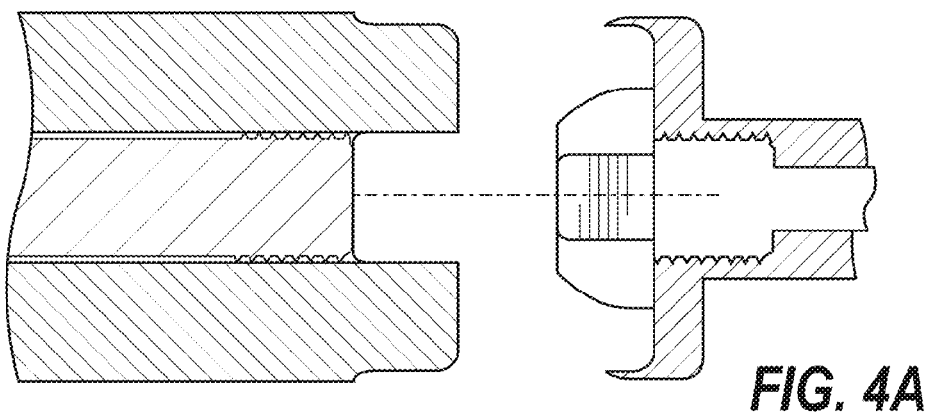
FIG. 4A is an example side view of the bone screw and screwdriver prior to engaging each other according to embodiments herein.
Figure 4B:
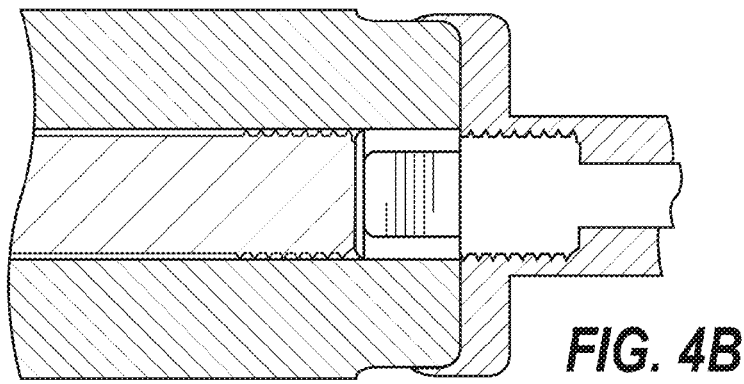
FIG. 4B is an example side view of the bone screw and screwdriver with force-transfer structure engaged, according to embodiments herein.
Figure 4C:
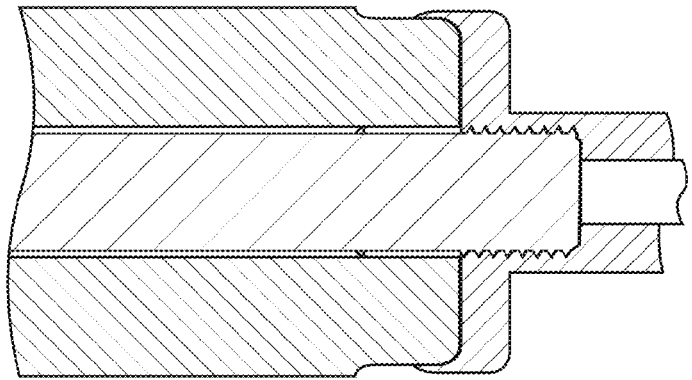
FIG. 4C is an example side view of the bone screw and screwdriver with force-transfer structure engaged as well as internal shaft secured to the bone screw, according to embodiments herein.

FIGS. 4A-4C shows progression of steps for engaging the active self-retaining mechanism. FIG. 4A shows a side sectional view of a tip of screwdriver 300 aligned with bone screw 200. In FIG. 4B, the screwdriver 300 and/or bone screw 200 have been moved so that the force receiving structure is in contact with the force transfer structure, but without the internal shaft extended. In FIG. 4C, the internal shaft has been manipulated or advanced so that external threading of the internal shaft engages with internal threading of the bone screw, thereby actively retaining the bone screw against the screwdriver.

In another embodiment, the bone screw and self-retaining driver system can include a compression mechanism that pushes the internal shaft towards the distal end of the external shaft of the driver. The compression mechanism essentially provides a linear pressure or force to the internal shaft (either directly or indirectly). There are various mechanisms that can be used as the compression mechanism, including a spring or band disposed within the handle of the driver. The spring can be positioned within the handle such that the spring pushes the internal shaft towards the distal end of the external shaft either by pushing or pulling the internal shaft. The screwdriver can also include an internal shaft release mechanism that enables removal of the internal shaft from bone screwdriver. In some example embodiments, the internal shaft release mechanism includes an end cap that removably engages with a proximal end of the handle portion. In this embodiment, the compression mechanism can include a spring located within the end cap.

Figure 7:
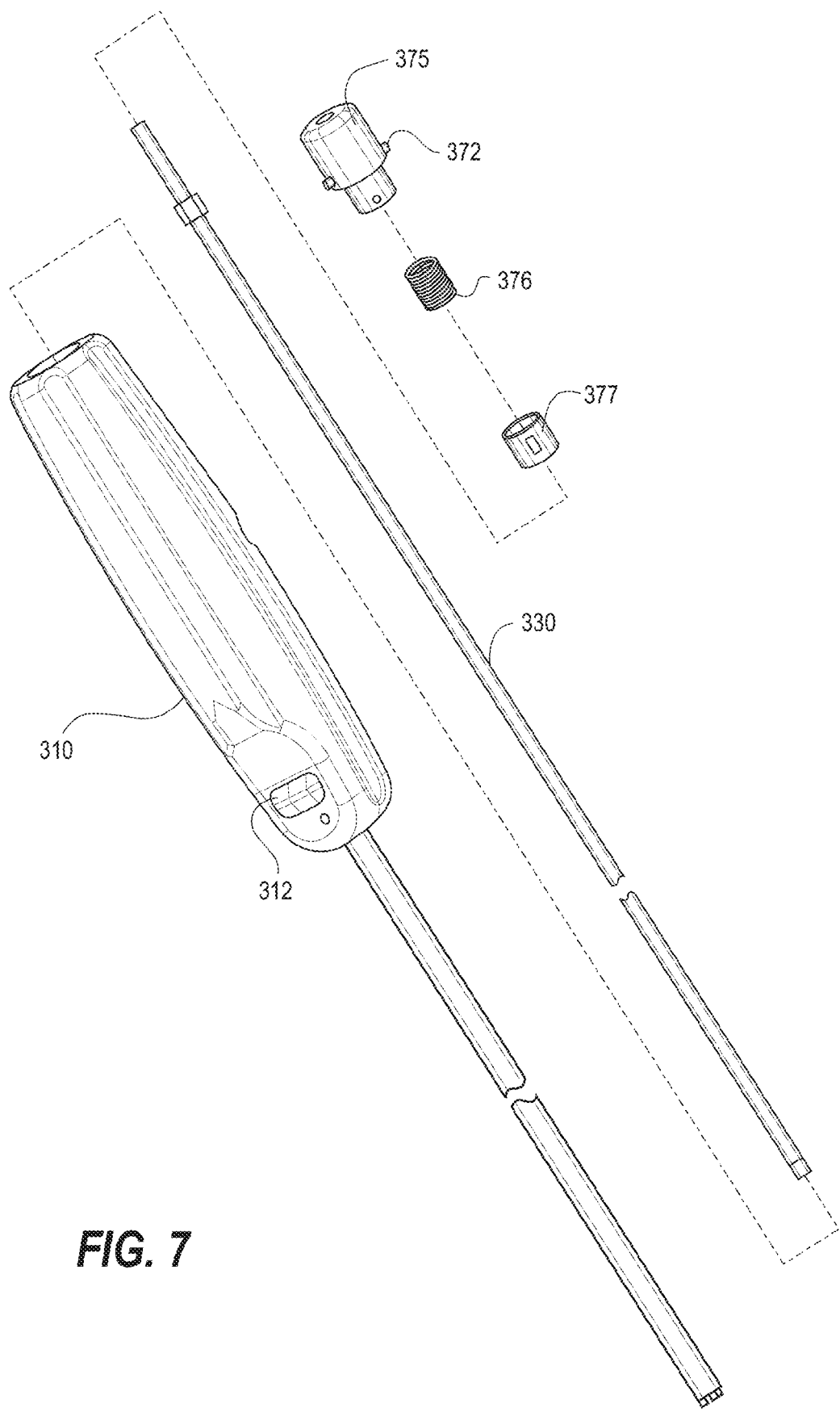
FIG. 7 is an example exploded perspective view of a self-retaining driver system for a bone screw according to embodiments herein.

FIGS. 5-7 illustrate an example embodiment of a compression mechanism and removable internal shaft assembly. FIG. 5 shows handle portion 310 and rotation mechanism 312, as well as end cap 375. Note that end cap 375 defines a lumen for receiving a guide wire. The handle portion also defines a J-pin groove 371 for receiving the end cap 375 and holding the end cap within the handle portion. For example, the end 375 can be inserted into the handle portion, rotated a distance, and then the end cap can pop-up and engage with the handle.

Referring to FIG. 6, a compression mechanism 370 is shown within handle portion 310. Also shown are end cap 375, hex drive 373, plunger 377, and spring 376. Thus, the end cap 375 defines a location for the spring 376 and plunger 377. When the end cap is inserted and secured or locked, the spring 376 can then supply a forward bias on the internal shaft via plunger 377. Plunger 377 travels with the spring and thus can in turn press on rotation mechanism 312. Internal shaft 330 can include a hex drive connection 373, which can be used by the rotation mechanism to impart rotational energy or torque to the internal shaft. The hex drive connection 373 can be welded onto the internal shaft or integral with it.

FIG. 7 shows an exploded view and illustrates how a new or cleaned internal shaft 330 can be inserted into the screwdriver, followed by the end cap 375 and accompanying spring 376 and plunger 377. Note that end cap 375 includes J-pins 372 for removably locking with the handle portion 310. With the end cap 375 locked, spinning the wheel/rotation mechanism causes the internal shaft to rotate and securely engage with Providing such a compression mechanism is beneficial during use, such as during a surgery. Without the compression mechanism, and with the internal shaft being slidably disposed within the external shaft, when a bone screw comes in contact with the screwdriver tip, the internal shaft will be pushed back into the external shaft. With such an apparatus, a user must simultaneously put forward pressure on the internal shaft (rotatable wheel) while the user is rotating the internal shaft using the wheel to engage the threads of the internal shaft. Since the internal shaft essentially floats within the external shaft, without a forward pressure, the internal shaft would rotate but would not engage the internal threads of the bone screw. Thus, the compression mechanism provides a spring bias so that the user only needs to rotate the internal shaft without providing forward pressure.

Providing a removable internal shaft can be beneficial for at least a couple of reasons. In some bone screwdriver applications, the internal shaft size can have a diameter size that translates to a relatively short fatigue life, at least compared to the fatigue life of the external shaft. An additional benefit is easy of cleaning. During surgery blood and fluids can travel between the external shaft and the internal shaft. When these two shafts have a relatively tight tolerance, then it becomes difficult to clean and sterilize the screwdriver assembly. Having a removable internal shaft, however, makes the assembly easier to clean and/or replace, and also enables use of disposable internal shafts.

Other embodiments include a method of fastening a bone screw to bone media using a bone screwdriver. This method includes removably securing a bone screw to a bone screwdriver. This bone screw comprising an elongated member having a distal end, a proximal end, and a longitudinal axis. At least a portion of the distal end has external threading adapted to advance the bone screw into bone media. The proximal end has a force-receiving structure configured to receive applied torque. The bone screw is cannulated by defining a passage that follows the longitudinal axis. The defined passage is sized to enable the bone screw to travel along a guide wire, such as a surgical guide wire. The proximal end defines a socket having internal threading. The defined socket is aligned with the defined passage. The bone screwdriver includes a shaft portion connected to a handle portion. The shaft portion includes an external shaft and an internal shaft. The internal shaft is positioned within the external shaft. The internal shaft is configured to rotate independent of the external shaft. A distal end of the external shaft has a force-transfer structure configured to transfer applied torque to the force-receiving structure of the bone screw when in contact with the force-receiving structure. A distal end of the internal shaft has external threading adapted to advance into the defined socket of the bone screw such that when advanced into internal threading of the defined socket, the bone screw is securely attached to the bone screwdriver via the internal shaft such that the force-transfer structure is in contact with the force-receiving structure. The handle portion includes a rotation mechanism that controls rotation of the internal shaft independent of the external shaft. The bone screwdriver is cannulated in that the bone screwdriver defines a passage or lumen or tube that follows a longitudinal axis of the bone screwdriver such that the bone screwdriver can travel along a guide wire. The method then includes removably securing the bone screw to the bone screwdriver by rotating the internal shaft to engage with the defined socket of the bone screw. Other active self-retaining mechanisms, that removably securing the bone screw to the bone screwdriver, can involve using a ball and socket mechanism or other active retaining device.

The method includes passing the secured bone screw and bone screwdriver along a surgical guide wire, advancing the bone screw into bone media or other media/tissue, and then releasing the internal shaft from the bone screw by rotating the internal shaft or otherwise disengaging an active retaining mechanism.

Another embodiment includes a bone screw and self-retaining driver system includes a bone screw and bone screwdriver. The bone screw, has an elongated member having a distal end, a proximal end, and a longitudinal axis, with at least a portion of the distal end having external threading adapted to advance the bone screw into bone media. The proximal end has a force-receiving structure configured to receive applied torque. The bone screw is cannulated in that the bone screw defines a passage that follows the longitudinal axis. The defined passage is sized to enable the bone screw to travel along a guide wire. The proximal end defines a socket configured to be secure with a driver securing mechanism. The defined socket is aligned with the defined passage.

The bone screwdriver has a shaft portion connected to a handle portion. The shaft portion includes an external shaft and an internal shaft. The internal shaft is positioned within the external shaft. The internal shaft is configured to rotate independent of the external shaft. A distal end of the external shaft has a force-transfer structure configured to transfer applied torque to the force-receiving structure of the bone screw when in contact with the force-receiving structure. A distal end of the internal shaft has a driver securing mechanism that secures the internal shaft to the defined socket of the bone screw such that the force-transfer structure is in contact with the force-receiving structure. The handle portion includes a rotation mechanism that controls rotation of the internal shaft independent of the external shaft. The bone screwdriver is cannulated in that it defines a passage that follows a longitudinal axis of the bone screwdriver such that the bone screwdriver can travel along a guide wire.

Those skilled in the art will also understand that there can be many variations made to the operations of the techniques explained above while still achieving the same objectives of the invention. Such variations are intended to be covered by the scope of this invention. As such, the foregoing description of embodiments of the invention is not intended to be limiting. Rather, any limitations to embodiments of the invention are presented in the following claims.

The invention claimed is:

1. A bone screw and self-retaining driver system comprising:
   a bone screw, the bone screw comprising:
      an elongated member comprising a head and a shaft extending distally from the head, the shaft further having a distal end, a proximal end, and a longitudinal axis,
      at least a portion of the distal end of the shaft having external threading adapted to advance the bone screw into bone media,
      the head defining a flange radially enlarged relative to the shaft of the bone screw, said flange having a proximal surface and a distal surface opposite to the proximal surface, the proximal surface comprising at least one recess defined by axial protrusions extending from the proximal surface configured to receive applied torque, and wherein the distal surface is concave relative to a peripheral annular edge of the distal surface;
      the bone screw being cannulated by defining a passage that follows the longitudinal axis of the bone screw, the defined passage sized to enable the bone screw to travel along a guide wire,
      the head and at least a portion of the proximal end of the shaft defining a socket having internal threading, the defined socket aligned with the defined passage; and
   a bone screwdriver, the bone screwdriver comprising:
      a handle portion;
      a shaft portion connected to the handle portion, the shaft portion including an external shaft and an internal shaft, wherein the internal shaft is positioned within the external shaft, and wherein the internal shaft is configured to rotate independent of the external shaft, at least one projection formed at a distal end of the external shaft, the at least one projection configured to transfer applied torque to the at least one recess of the head of the bone screw when in contact with the at least one projection, an external threading formed at a distal end of the internal shaft, the external threading adapted to advance into the defined socket of the bone screw such that, when advanced into the internal threading of the defined socket, the bone screw is securely attached to the bone screwdriver via the internal shaft and the at least one projection of the external shaft is in contact with the at least one recess of the head of the bone screw, a rotatable wheel that controls rotation of the internal shaft independent of the external shaft, wherein the rotatable wheel is secured within the handle portion at a longitudinal position distally offset from a proximal end of the handle portion and wherein the rotatable wheel is independent from the inner shaft, the bone screwdriver being cannulated by defining a passage that follows a longitudinal axis of the bone screwdriver such that the bone screwdriver can travel along a guide wire;

wherein the rotatable wheel is framed within an opening defined within the handle portion and is configured to slide longitudinally within the handle, causing the internal shaft to travel longitudinally within the external shaft, and wherein a longitudinal travel of the rotatable wheel is sufficient for the internal shaft to retract within the external shaft and to extend from the external shaft to couple with the defined socket.

2. The bone screw and self-retaining driver system of claim 1, wherein the at least one recess of the head of the bone screw includes at least two slots that receive a corresponding one of the at least one projection of the bone screwdriver.

3. The bone screw and self-retaining driver system of claim 1, wherein the at least one recess of the head of the bone screw includes a recessed structure having a shape that corresponds to the at least one projection of the bone screwdriver.

4. The bone screw and self-retaining driver system of claim 1, wherein the bone screwdriver being cannulated includes the internal shaft being cannulated as well as the handle portion being cannulated such that the defined passage follows a same axis through the handle portion and the internal shaft.

5. The bone screw and self-retaining driver system of claim 1, wherein the defined socket is centered with the at least one recess of the head of the bone screw.

6. The bone screw and self-retaining driver system of claim 5, wherein the defined socket and the defined passage of the bone screw are aligned to have a same axis as the longitudinal axis of the bone screw.

7. The bone screw and self-retaining driver system of claim 1, wherein the external shaft defines a longitudinal space within which the internal shaft rotates.

8. The bone screw and self-retaining driver system of claim 1, wherein the bone screwdriver further comprises: a compression mechanism that pushes the internal shaft towards the distal end of the external shaft.

9. The bone screw and self-retaining driver system of claim 8, wherein the compression mechanism includes a spring disposed within the handle, the spring pushing the internal shaft towards the distal end of the external shaft.

10. The bone screw and self-retaining driver system of claim 1, wherein the bone screwdriver further comprises an internal shaft release mechanism that enables removal of the internal shaft from bone screwdriver.

11. The bone screw and self-retaining driver system of claim 10, wherein the bone screwdriver further comprises: a compression mechanism that pushes the internal shaft towards the distal end of the external shaft.

12. The bone screw and self-retaining driver system of claim 11, wherein the internal shaft release mechanism includes an end cap that removably engages with a proximal end of the handle portion, wherein the compression mechanism includes a spring located within the end cap.

13. The bone screw and self-retaining driver system of claim 1, wherein the internal shaft extends through a longitudinal extent of the rotatable wheel along the longitudinal axis of the bone screwdriver, and wherein a portion of the internal shaft proximal to the rotatable wheel is positioned within a portion of the cannulation extending through the handle portion.

* * * * *